United States Patent [19]
Koyama et al.

[11] Patent Number: 4,768,383
[45] Date of Patent: Sep. 6, 1988

[54] METHOD OF PREDICTING REMAINING LIFETIME OF METAL MATERIAL

[75] Inventors: Teruo Koyama; Kohji Tamura, both of Kure, Japan

[73] Assignee: Babcock-Hitachi Kabushiki Kaisha, Tokyo, Japan

[21] Appl. No.: 109,163

[22] Filed: Oct. 16, 1987

[30] Foreign Application Priority Data

Oct. 16, 1986 [JP] Japan ................................. 61-246149

[51] Int. Cl.⁴ ........................................... G01N 21/00
[52] U.S. Cl. ..................................................... 73/787
[58] Field of Search ................. 73/783, 787, 760, 822, 73/865.8, 865.9, 104; 378/72; 376/249

[56] References Cited

U.S. PATENT DOCUMENTS 2,462,374  2/1949  Firth ...................................... 378/72

FOREIGN PATENT DOCUMENTS 120585 10/1978 Japan .
 60248  4/1983 Japan .
201066 11/1983 Japan .

*Primary Examiner*—Jerry W. Myracle
*Attorney, Agent, or Firm*—Antonelli, Terry & Wands

[57] ABSTRACT

Disclosed is a method of predicting the remaining lifetime of a metal material, wherein the shapes of grains of the metal material are quantitatively measured to obtain variations in the shapes of the grains, and the remaining lifetime of the metal material is predicted on the basis of the variations. In accordance with the present invention, it is possible to statistically arrange the variations in the shapes of the grains by measuring such variations sequentially in time.

5 Claims, 7 Drawing Sheets

DIRECTION OF STRESS
FIG. 1a
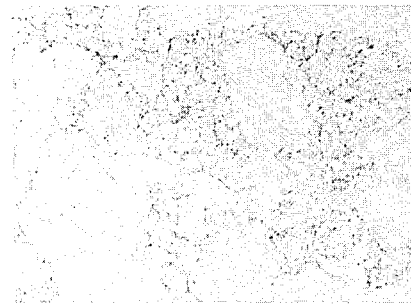
FIG. 1b
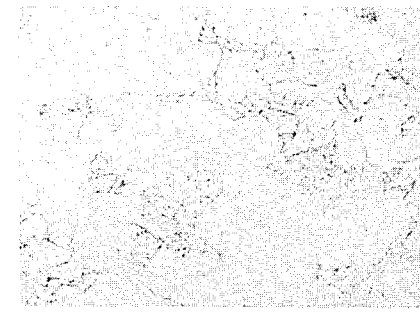
FIG. 1c
25μm

F I G. 2
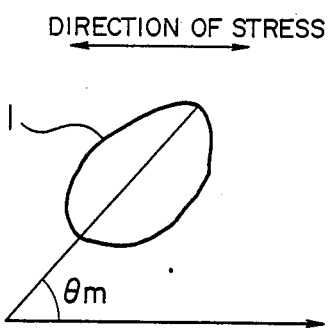
F I G. 3a
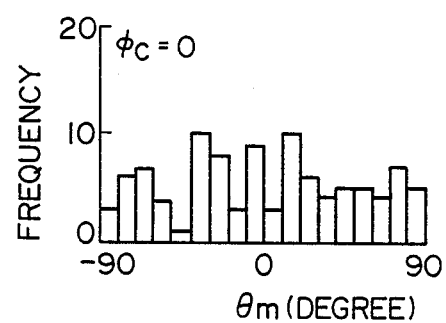
F I G. 3b
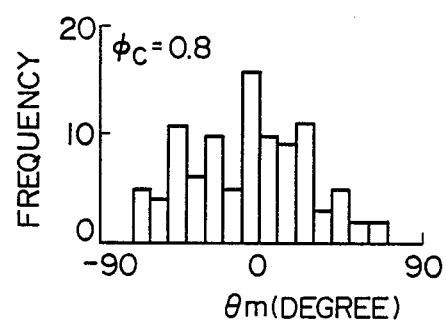

25μm

F I G. 10
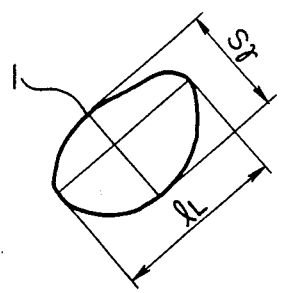
F I G. 11
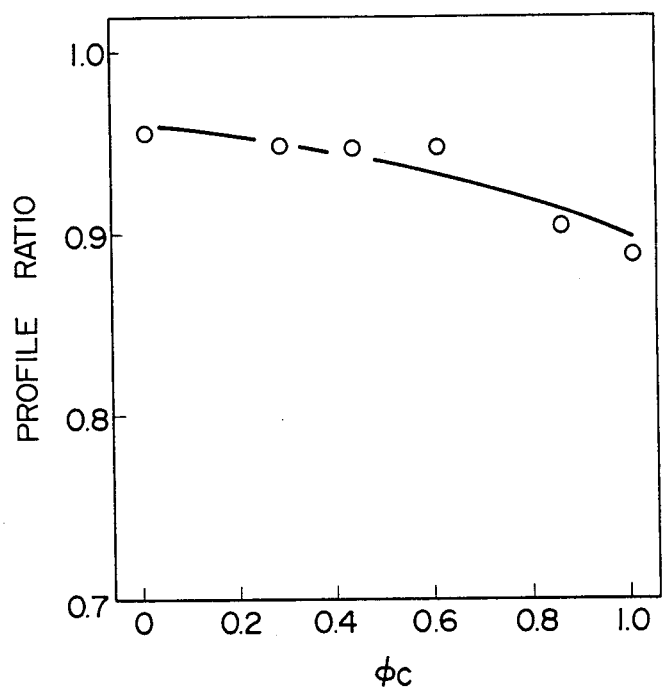

METHOD OF PREDICTING REMAINING LIFETIME OF METAL MATERIAL

BACKGROUND OF THE INVENTION

1. Field of the Invention

The present invention relates to a method of predicting the remaining lifetime of a metal material and, more particularly, to a method of predicting the remaining lifetime of a metal material which is normally used for a boiler or the like and which suffers creep damage due to being used under high pressure at high temperature.

2. Description of the Related Art

It is well known that, in equipment used under high pressure at high temperature for a long time, as for example in thermal power plant or chemical plant, materials used for components of such actual equipment may suffer creep damage, thereby deteriorating the quality of material while the equipment is in operation. Such deterioration in the quality of material is dominated by such factors as metal temperature, working stress and operating period. In the case of boilers for thermal power plants, it is therefore common practice to determine the quality and size of material to be used by considering those dominant factors, so as to ensure a lifetime normally equivalent to one hundred thousand hours (about fifteen years in the case of normal operation).

However, in such boilers such an accident frequently occurs that the material is damaged in several tens of thousands of hours. It is considered that this accident is caused by an unexpected rise in metal temperature owing to drift, etc. of combustion gas and an abnormal deterioration in the quality of material owing to segregation in the material, e.g., sigma phase embrittlement, etc. Also, the number of power plants which exceed the design lifetime of one hundred thousand hours has recently been increasing. In addition, since an atomic power plant is operated under a base-load condition, the plant is expected to be exposed to severe operating conditions such as an intermediate-load operation and an everyday repetition of start and stop. For these reasons, it has become necessary to develop techniques which enable extension of the lifetime of the plant by exactly predicting the remaining lifetime of the material and proposing the timing of repair and replacement.

Methods of detecting the deterioration in the quality of material are classified into two major types; namely, destructive methods and nondestructive methods. Destructive methods are methods of predicting a remaining lifetime by sampling a portion of a component of an actual equipment, followed by a micrography, a tensile test, a creep test, an impact test and so on, in combination with a stress analysis. The following predicting method using metal structure samples of a material is known as a typical example of a destructive method. Namely, in this method a number of standard metal structures are previously produced under various laboratory conditions and they are compared with a metal structure sample taken from a constituent member of an actual equipment, thereby predicting the lifetime of the material of the member (see, for example, *Nippon Kokan Gijutsu* No. 62, Pages 531 to 558). An index utilized in this method is the decomposition and agglomeration of a pearlite in the case of Cr-Mo steel while, in the case of stainless steel, the precipitation and agglomeration of carbide in grain boundary and within grain or the state of precipitation of a sigma phase is utilized as the index. For example, there is a technique of predicting the remaining lifetime of stainless steel SUS 321 from the relationship between the quantity of precipitation of the sigma phase and the creep damage in that steel (see Japanese Patent Application Laid-Open Publication No. 201066/83 and *Karyoku Genshiryoku Hatsuden* Vol. 33, No. 9, Pages 899 to 912). There is another technique of predicting the remaining lifetime from the number of voids produced by creep. (See *Zairyo* Vol. 28, No. 308, Pages 372 to 378).

The aforesaid prediction method utilizing the quantitative determination of the sigma phase is effective but involves the following problems. Namely, the kind of material which can be handled in this method is limited to stainless steel or high Cr steel, and the state of precipitation of the sigma phase varies even in the same stainless steel owing to a slight difference in chemichal composition. Further, a prediction method utilizing the quantitative determination of a creep cavity is effective but involves also the following problems. Namely, the kind of material which can be handled in this method is limited to a material of low transgranular ductility, such as stainless steel or high Cr steel (for example, HK 40), so that it is difficult to apply this method to a material of high transgranular ductility such as low alloy steel for boilers, because creep cavities are difficult to be formed in that material.

Nondestructive methods are methods of indirectly predicting a remaining lifetime by detecting change in a metal structure, such as the decomposition owing to heating or creep, and physical change owing to formation of voids.

In this case, various kinds of physical quantities are available, and the following items have already been put into practical use or under study: namely, for example, electrical resistance (Japanese Patent Application Laid-Open Publication No. 60248/83), ultrasonic sound speed (Japanese Patent Application Laid-Open Publication No. 120585/78), and misorientation by X-ray and coil impedance by eddy current (Japanese Patent Application Laid-Open Publication No. 88781/78).

The nondestructive methods generally involve the following problems. Firstly, a high-precision device is needed since extremely slight changes must be detected in order to detect variations in physical quantities such as electrical resistance which might be caused by microscopic changes in the structure of a metal material. Further, there is a possibility that a large error may occur due to the handling of the device, the measurement environment and so on. In particular, unlike turbines, boilers are commonly placed in an adverse measurement environment, and this makes it difficult to perform accurate measurement. In addition, turbines are generally made of a material, such as Cr-Mo-V steel, having a high carbon content, so that the physical quantities such as electrical resistance decrease to a significant extent. On the other hand, since boilers are made of a material, such as $2\cdot\frac{1}{4}$ Cr - 1 Mo steel, having a low carbon content, the physical quantities don't greatly decrease, and this makes it difficult to perform satisfactory evaluation. Secondly, in these nondestructive methods, a master curve is previously produced under laboratory conditions and it is compared with the result of measurement of a component of an actual equipment to predict the remaining lifetime of that component. However, physical quantities to be measured are obtained by detecting extremely slight changes in a material, and the absolute values of the physical quantities vary in compliance with changes in an initial state of the material or merely in heating conditions. For this reason, the degree of damage must be evaluated on the basis of a relative value between the physical quantity of a damaged material and that in the initial state of the material before damage or in a merely heated state, not on the basis of the absolute value of the physical quantity. Therefore, when the master curve is to be produced under laboratory conditions, it is necessary to use a material the initial state of which is the same as that of a component of a actual equipment whose lifetime is to be measured, that is, to use a material of the same charge. In the present circumstances, however, it is impossible to obtain the materials from which boilers currently in operation (in particular, boilers produced ten or more years ago) were produced. Moreover, the data for structure, hardness and short-time tensile test might be obtained as the data of the material at that time, but it is virtually impossible to obtain the data for various physical quantities to be utilized in evaluation of the lifetime. Further, since previous methods of producing materials at that time differ from current methods, it is very difficult to reproduce the materials at that time.

Accordingly, the aforesaid prior art further involves the following problems.

In the destructive methods, it is the most reliable method to predict a remaining lifetime by subjecting a sample taken from a component of an actual equipment to a creep test. However, this method needs enormous costs and time and, in addition, a range inspected by this method is restricted. Also, in the method utilizing structure observation, rapid evaluation is enabled, but quantitative evaluation is difficult to perform since the evaluation is conducted by comparison with standard photomicrographs.

In addition, the change in structure is dominated mainly by temperature and time, but the effect of stress is small. For this reason, it is difficult to directly associate the creep damage with the change in structure.

In the nondestructive methods, there is a possibility that an error may occur because extremely slight changes in physical quantity of a material used are measured, and since the physical quantity varies due to environmental temperature etc., it is difficult to strictly compare the physical quantity with a master curve produced under laboratory conditions. In particular, it is impossible to obtain the data for materials produced ten or more years ago, and it is also difficult to reproduce such materials. Accordingly, both the destructive and nondestructive methods involve a number of problems.

SUMMARY OF THE INVENTION

It is therefore an object of the present invention to provide a method of directly and simply predicting the remaining lifetime of a metal material by observing a material constituting a component of an actual requirement.

The above object is achieved by the present invention which is constructed such that, by quantitatively measuring the shapes of grains of the metal material, the remaining lifetime is predicted on the basis of the variations in the shapes of grains.

In accordance with the present invention, since the grains are deformed by being elongated in a direction in which stress acts when the metal material suffers creep damage, it is possible to statistically arrange the variations in the shapes of grains of a metal material by measuring such variations sequentially in time.

As a method of measuring grains, a sample is taken from a component of an actual equipment or, alternatively, nondestructive observation using a replica method is effected to obtain a standard deviation as a variation in the shape on the basis of, for example, the distribution of angles which the direction of stress makes with the axis of the maximum length of the grains.

BRIEF DESCRIPTION OF THE DRAWINGS

FIG. 1a is a photomicrograph showing the metal structure of a non-used material of 2·¼ Cr - 1 Mo steel;

FIG. 1b is a photomicrograph showing the metal structure of a merely heated material (creep damage rate $\phi c=0$);

FIG. 1c is a photomicrograph showing the metal structure of a material which suffered creep damage (creep damage rate $\phi c=0.8$);

FIG. 2 is a view used for explaining a method of measuring a parameter $\theta m$ indicative of variations in the shape of a grain, in accordance with the present invention;

FIGS. 3a and 3b are graphs showing the distribution of $\theta m$ corresponding to FIGS. 1b and 1c, respectively;

FIG. 10 is a view used for explaining a method of measuring parameters $l_L$ and $l_S$ indicative of variation in the shape of a grain, in accordance with the present invention; and FIG. 11 is a graph showing the relationship between a creep damage rate and a profile ratio used as a parameter indicative of variations in the shapes of grains, in accordance with the present invention.

DESCRIPTION OF THE PREFERRED EMBODIMENT

Figure 4:
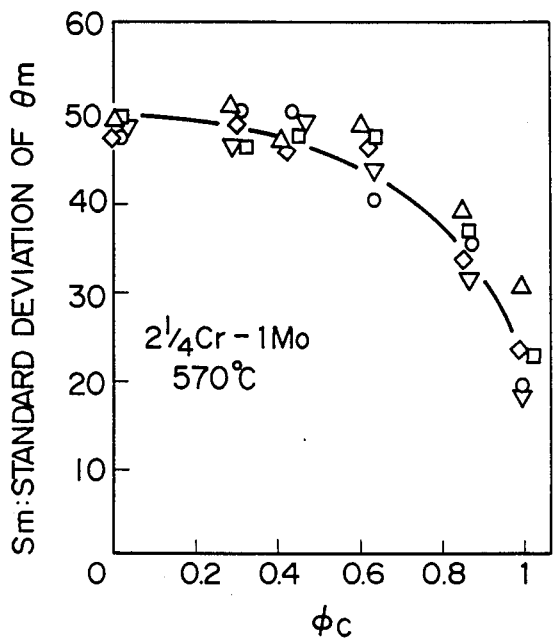
FIG. 4 is a graph showing the relationship between a standard deviation Sm of the distribution of $\theta m$ and a creep damage rate.

A preferred embodiment of the present inivention will be described below with reference to FIGS. 1a to 11. In this embodiment, the prediction method of the invention is applied to 2·¼ Cr - 1 Mo steel which is a typical material for boilers.

As shown in FIGS. 1a to 1c, when the grains of a metal material suffer creep damage, each grain 1 is elongated in a direction in which the stress acts. Therefore, the shape of the grain is measured to detect the degree of a deterioration in the metal material on the basis of variations in the shape of the grain, thereby predicting the remaining lifetime of the material.

In general, when a metal material suffers creep damage, the grains of the material are subjected to creep deformation. In other words, the creep deformation can be understood as the accumulation of the deformation of each grain. Therefore, the creep damage can be detected by measuring the deformation of each grain sequentially in time. When deformed due to creep, the grain is gradually elongated in the direction in which stress acts. It is therefore possible to detect creep damage by arranging with parameters indicative of the degree of elongation of the grain. Further, if the material having been rolled in a production process is subjected to a final heat treatment the grains are substantially balanced in regular polygon although the grain size differs in dependence on heat treatment condition and chemical composition, so that the variations in the shape of each grain is not affected by the quality of material, the heat treatment condition and the like. In other words, the variations in the shape of each grain correspond directly to creep damage and it is therefore unnecessary to consider the initial state or the merely heated state of the material.

FIGS. 1a to 1c show the metal structures of 2-¼ Cr - 1 Mo steel. FIG. 1a shows the metal structure of a non-used material, FIG. 1b the metal structure of a merely heated material (creep damage rate $\phi_c=0$), and FIG. 1c the metal structure of a material which suffered creep damage (creep damage rate $\phi_c=0.8$). As can be seen from these metal structures, a significant amount of pearlite is decomposed in the merely heated material and the creep-damaged material, but the influence of the difference in creep damage rate $\phi_c$ therebetween is not observed. However, in the creep-damaged material, the grains are elongated in the direction in which stress acts. It is to be noted that the creep damage rate $\phi_c$ is given by the following equation under the conditions that the same material is used at a constant creep test temperature:

$$\phi_c = t/t_r$$

where $t_r$ represents the creep rupture time and t represents the elapsed time in the creep test.

The present inventors noticed the abovementioned point, and using a picture processor they studied the shapes of grains of materials variously damaged. FIG. 2 shows a method of measuring a parameter representative of the shape of a grain. As shown, calculations are performed on an angle $\theta m$ which the axis of maximum length of the grain makes with the direction in which stress acts.

FIGS. 3a and 3b show the distributions of $\theta m$ corresponding to FIGS. 1b and 1c, respectively, in which grains measured are one hundred in number. In the case of the creep damage rate $\phi_c$ is zero as shown in FIG. 3a, since the shape of each grain is close to a regular polygon, $\theta m$ may correspond to any angle and therefore the distribution of $\theta m$ is substantially flat. In contrast, if the creep damage rate $\phi_c$ is 0.8 as shown in FIG. 3b, since the grain is elongated in the direction in which stress acts, the distribution of $\theta m$ shows a normal distribution whose peak appears in the direction of stress ($\theta m = 0°$).

In order to represent the difference between these distributions of $\theta m$, a standard deviation Sm is calculated, and the resultant relationship between the creep damage rate $\phi_c$ and the standard deviation Sm is shown in FIG. 4. As can be seen from FIG. 4, as the creep damage rate $\phi_c$ increases, the value of Sm decreases. In particular, when the creep damage rate $\phi_c$ becomes greater than 0.5 the value of Sm decreases remarkably, so that it becomes easy to predict the remaining lifetime on the basis of this parameter. This graph may be employed to evaluate the degree of creep damage in a component of an actual equipment. Further, using various kinds of non-used materials and merely heated materials the values of Sm were found in the cases where their creep damage rates were zero, but in any case the value of Sm was around 50 and the dispersion thereof was small, and therefore the influences of chemical composition and heat treatment were not observed. In other words, according to the present method it is possible to directly evaluate the creep damage without requiring the data for non-used material or merely heated material.

For the following reason, one hundred grains were utilized for measurement of $\theta m$. It is conceptually conceivable that the shapes of the grains vary with time. However, as is evident in FIGS. 1a and 1b, even if each grain is observed, it is impossible to clearly detect the variations in the shape of the grain. Therefore, it becomes necessary to increase the number of grains to be measured by a machine having no personal error and to utilize a statistic method. From various studies on the number of grains to be measured, it was made clear that when eighty or more grains were measured the dispersion in the value of Sm decreased, so that the number of measured grains did not affect the result. Thus, it was determined to utilize one hundred grains taking a margin into consideration.

Figure 5A:
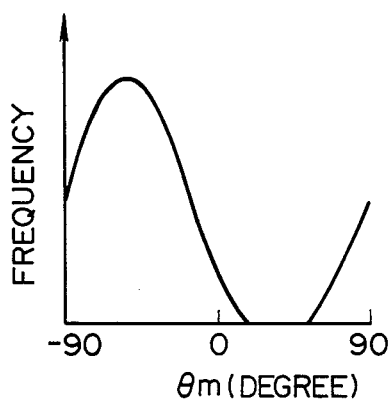
FIG. 5a is a graph showing one example of the distribution of $\theta m$ when the direction of stress is known.
Figure 5B:
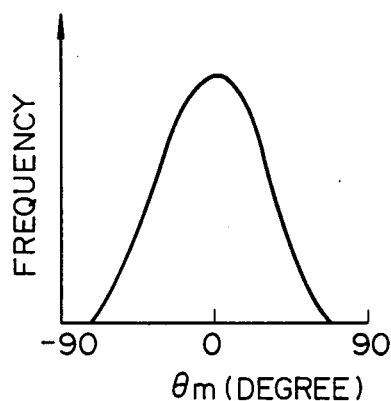
FIG. 5b is a graph showing one example of the distribution of $\theta m$ when the direction of stress is unknown.
Figure 6:
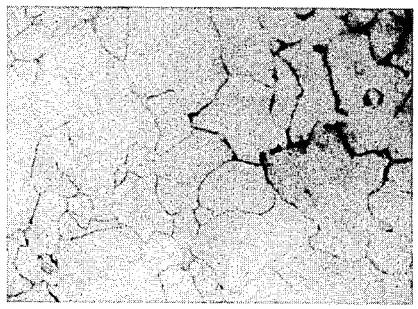
FIG. 6 is a photomicrograph of one example of a metal structure in accordance with a replica method.

Since the material shown in this embodiment is variously damaged by creep tests, the direction of stress is clearly detected. However, in a component of an actual equipment, there is a case where the direction of stress is not clearly detected. Therefore, even in a case where the degree of creep damage is high, the distribution of $\theta m$ takes such a shape as shown in FIG. 5a. This is because an optional angle is assumed to be the direction of stress. Although the standard deviation of this distribution becomes remarkably large, if the continuity of angles is considered (90° and −90° correspond to the same direction), it will be understood that FIGS. 5a and 5b show the same distribution. Therefore, the angle is shifted one degree at a time (that is, the distribution of FIG. 5a is converted into that of FIG. 5b), the distribution of $\theta m$ whose standard deviation becomes minimum is obtained and that standard deviation is employed as Sm of the material. By means of using this method, an advantage is obtained that the direction of the maximum stress in a component of an actual equipment can be detected, vice versa. Further, in this embodiment, the shape of the grain is measured by directly observing a sample, but as shown in FIG. 6 the shapes of grains can be clearly observed by using a replica method in which the structure of an actual object is transferred to a thin film, so that it is possible to perform completely the same evaluation as that of the above-described embodiment.

Figure 7:
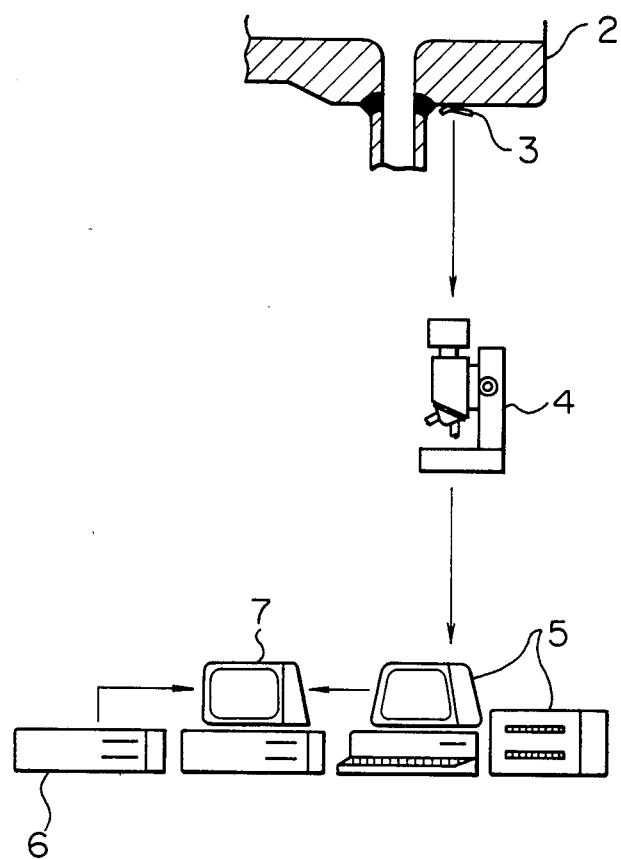
FIG. 7 is a block diagram showing the procedure of predicting a remaining lifetime on the basis of the shapes of grains in a component of an actual equipment.

FIG. 7 illustrates a typical example of the procedure of applying the present method to a component of an actual equipment. In this example, a thin film is sampled by a replica method since, in principle, a nondestructive method is applied to a component 2. It will be appreciated, however, that even if replica sampling is possible the accuracy of measurement is rather improved by taking samples. In the replica method, a portion to be evaluated is polished by a grinder or the like, and the thus-polished portion is etched by an etchant suitable for the material. In this case, it is preferable to continue etching for a somewhat longer time in order to clarify the shapes of the grains. A replica film 3, which is partially melted by a solvent, is stuck to the thus-etched portion. When the replica film 3 is peeled therefrom after dried, the surface structure of the portion is transferred to the replica film 3. The replica film 3 is observed with a microscope 4 and the shapes of the grains are measured by an image processor 5 to calculate the standard deviation Sm as a damage parameter. Then, a personal computer 7 is used to calculate and evaluate the remaining lifetime of the material on the basis of the relationships between this Sm, Sm stored in a previously prepared data base 6 and the degree of creep damage.

It was confirmed that, although based on the same concept, the following items were effective as a parameter for quantitatively determining variations in the shapes of grains.

Figure 8:
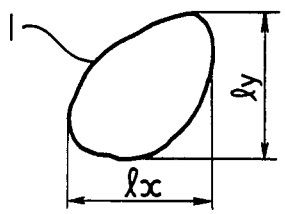
FIG. 8 is a view used for explaining a method of measuring parameters $l_x$ and $l_y$ indicative of variations in the shape of a grain, in accordance with the present invention.

(a) Relationship between Length and Width of Grain:

As shown in FIG. 8, a length $l_x$ projected to the axis in the direction of stress and a width $l_y$ projected to the axis perpendicular to the direction of the stress are measured. Then, the relationship between the average of a ratio $l_x/l_y$ and the creep damage rate $\phi c$ is obtained.

Figure 9:
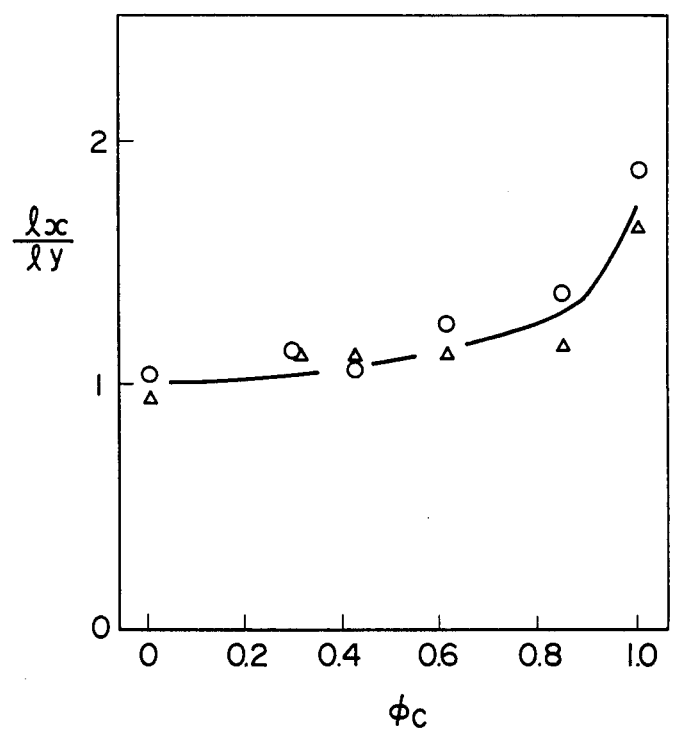
FIG. 9 is a graph showing the relationship between $l_x/l_y$ and a creep damage rate, in accordance with the present invention.

FIG. 9 shows the thus-obtained result. As clearly shown in FIG. 9, as the creep damage rate $\phi c$ increases, the value of $l_x$ becomes larger than that of $l_y$ and therefore the value of the ratio $l_x/l_y$ increases. Accordingly, the lifetime of a material can be predicted, employing the value of $l_x/l_y$ as a parameter. Further, as shown in FIG. 10, if a ratio of a maximum length $l_L$ of each grain to a maximum width $l_S$ of an axis perpendicular to the length, that is, a ratio $l_L/l_S$ is used as a parameter, a graph having a tendency similar to that of FIG. 9 can be obtained.

(b) Degree of Roundness:

The degree of roundness of each grain is a parameter which enables estimation of the degree of creep damage. The degree of roundness is represented by various methods, and one example thereof is the use of a profile ratio. The profile ratio is represented by (the circumferential length of an equivalent circle)/(the circumferential length of a grain). FIG. 11 shows the relationship between the profile ratio and the creep damage rate $\phi c$. As is evident from FIG. 11, prediction as to the degree of creep damage is also enabled from the profile ratio. As another example of the parameter representing the degree of roundness, (circumferential length)$^2$/(area) is available. The reason why the degree of roundness is usable as a parameter is that, although the shape of a grain is close to a circle when the damage is small, as the damage becomes large, the grain is elongated in the direction of stress to increase the degree of roundness.

It is to be noted that the parameter referred to as another example does not greatly vary in accordance with variations in the creep damage rate $\phi c$, so that the accuracy of measurement decreases. However, such a parameter may be effective in measuring a different kind of material.

In accordance with the present invention, the shapes of the grains of a metal material are quantitatively measured and the thus-obtained variations are compared to enable quantitative prediction as to the remaining lifetime of the metal material, in a simple way and by a nondestructive method. This enables a great reduction in cost and time and eliminates the need to use a high precision device. In addition, it is unnecessary to employ data for the initial state of materials and for merely heated materials, and the inventive method can also be applied to various polycrystalline metal materials. It will be readily understood from the above description that the present invention possesses a variety of industrial merits.

What is claimed is:

1. A method of predicting the remaining lifetime of a metal material comprising:
   quantitatively measuring the shapes of grains of said metal material;
   obtaining variations in said shapes of said grains; and
   predicting the remaining lifetime of said metal material on the basis of said variations.

2. The method according to claim 1, wherein said variations in said shapes are represented by a standard deviation of the distribution of angles which the direction of stress makes with the direction of the longitudinal axis of the maximum diameter of each of said grains.

3. The method according to claim 1, wherein said variations in said shapes are represented by a ratio of the maximum length of the longitudinal axis of each of said grains to the maximum width of an axis of each of said grains perpendicular to said longitudinal axis.

4. The method according to claim 1, wherein said variations in said shapes are represented by a ratio of the length of the longitudinal axis of each of said grains in the direction of stress to the width of each of said grains in the direction perpendicular to said direction of stress.

5. The method according to claim 1, wherein said variations in said shapes are represented by the degree of roundness of each of said grains.

* * * * *